United States Patent [19]

Maienfisch et al.

[11] Patent Number: 4,778,809
[45] Date of Patent: Oct. 18, 1988

[54] 5-ESTERS OF MILBEMYCINS FOR CONTROLLING PARASITIC PESTS

[75] Inventors: Peter Maienfisch; Elmar Sturm, both of Aesch, Switzerland

[73] Assignee: Ciba-Geigy Corporation, Ardsley, N.Y.

[21] Appl. No.: 895,979

[22] Filed: Aug. 13, 1986

[30] Foreign Application Priority Data

Aug. 23, 1985 [CH] Switzerland ............... 3642/85

[51] Int. Cl.$^4$ ................ C07D 493/22; A61K 31/365
[52] U.S. Cl. .................................... 514/450; 549/264
[58] Field of Search .................... 549/264; 514/450

[56] References Cited
FOREIGN PATENT DOCUMENTS
0142969 5/1985 European Pat. Off. .

Primary Examiner—Norma S. Milestone
Attorney, Agent, or Firm—Edward McC. Roberts; Meredith C. Findlay

[57] ABSTRACT

The invention relates to ecto- and endoparasitic milbemycins of formula I

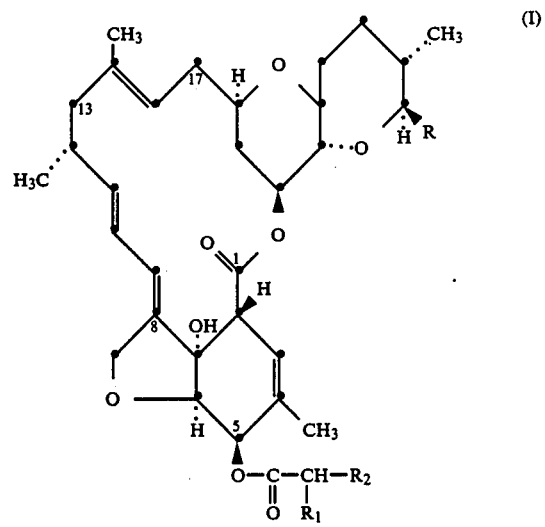

wherein
R is methyl, ethyl, isopropyl or sec-butyl;
$R_1$ is hydrogen, fluorine or $C_1$-$C_4$ alkyl;
$R_2$ is one of the groups

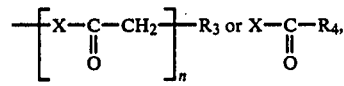

n is a value from 2 to 6;
X is oxygen or sulfur;
$R_3$ is halogen; and
$R_4$ is hydrogen, $C_1$-$C_{12}$ alkoxy, $C_3$-$C_7$cycloalkoxy or $C_2$-$C_6$alkenyloxy; or $C_1$-$C_{18}$alkyl which is unsubstituted or substituted by halogen, $C_1$-$C_4$alkoxy, hydroxy and/or COOG, G being hydrogen, an alkali metal cation or an alkaline earth metal cation; or $R_4$ is $C_3$-$C_7$cycloalkyl which is unsubstituted or substituted by halogen and/or $C_1$-$C_4$alkyl;
$C_2$-$C_{18}$alkenyl which is unsubstituted or substituted by halogen;
$C_2$-$C_{18}$alkynyl which is unsubstituted or substituted by halogen;
phenyl which is unsubstituted or substituted by halogen, $C_1$-$C_4$alkyl $C_1$-$C_4$alkoxy, nitro, cyano and/or $C_1$-$C_4$haloalkyl; or a 5- or 6-membered unsaturated or saturated heterocyclic ring system which contains one to three hetero atoms selected from the series consisting of nitrogen, oxygen and sulfur and which is unsubstituted or substituted by oxo and/or by one to three substituents selected from halogen, $C_1$-$C_4$alkyl, $C_1$-$C_4$alkoxy and/or $C_1$-$C_4$haloalkyl;
to the use thereof in agriculture and to the preparation thereof by esterifying the 5-OH-milbemycins on which they are based.

11 Claims, No Drawings

5-ESTERS OF MILBEMYCINS FOR CONTROLLING PARASITIC PESTS

The present invention relates to milbemycin derivatives of formula I below which are esterified in the 5-position, to the preparation of these compounds and to the use thereof for controlling pests such as ecto- and endoparasites, in particular nematodes. The invention further relates to pesticidal compositions which contain at least one of these compounds as active ingredient.

The compounds of the present invention are characterised by the formula I

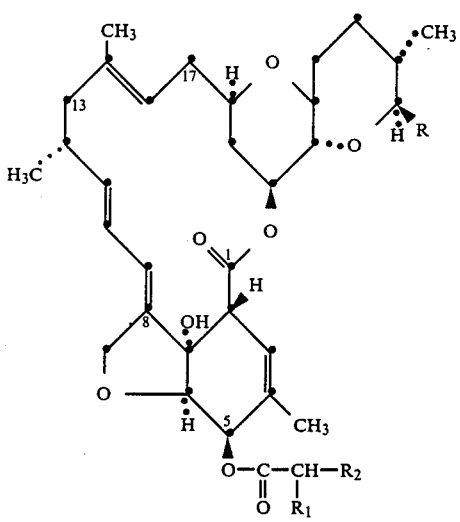

wherein
R is methyl, ethyl, isopropyl or sec-butyl;
$R_1$ is hydrogen, fluorine or $C_1$–$C_4$ alkyl;
$R_2$ is one of the groups

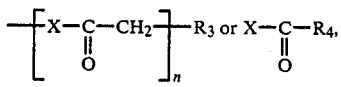

in which formulae
n is a value from 2 to 6;
X is oxygen or sulfur;
$R_3$ is halogen; and
$R_4$ is hydrogen, $C_1$–$C_{12}$alkoxy, $C_3$–$C_7$cycloalkoxy or $C_2$–$C_6$alkenyloxy; or $C_1$–$C_{18}$alkyl which is unsubstituted or substituted by halogen, $C_1$–$C_4$alkoxy, hydroxy and/or COOG, G being hydrogen, an alkali metal cation or an alkaline earth metal cation; or $R_4$ is $C_3$–$C_7$cycloalkyl which is unsubstituted or substituted by halogen and/or $C_1$–$C_4$alkyl; $C_2$–$C_{18}$alkenyl which is unsubstituted or substituted by halogen; $C_2$–$C_{18}$alkynyl which is unsubstituted or substituted by halogen; phenyl which is unsubstituted or substituted by halogen, $C_1$–$C_4$alkyl $C_1$–$C_4$alkoxy, nitro, cyano and/or $C_1$–$C_4$haloalkyl; or a 5- or 6-membered unsaturated or saturated heterocyclic ring system which contains one to three hetero atoms selected from the series consisting of nitrogen, oxygen and sulfur and which is unsubstituted or substituted by oxo and/or by one to three substituents selected from halogen, $C_1$–$C_4$alkyl, $C_1$–$C_4$alkoxy and/or $C_1$–$C_4$haloalkyl.

Depending on the number of carbon atoms indicated, alkyl by itself or as moiety of another substituent will be understood as meaning for example the following straight chain groups: methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl etc. and the branched isomers thereof, e.g. isopropyl, isobutyl, tert-butyl, isopentyl etc. Alkenyl by itself or as moiety of an alkenyloxy group is e.g. propen-1-yl, allyl, buten-1-yl, buten-2-yl, buten-3-yl etc. Alkynyl is for example ethynyl, propyn-1-yl, propargyl, butyn-1-yl etc. Throughout this specification, halogen will be understood as meaning fluorine, chlorine, bromine or iodine, with chlorine or bromine being preferred. Cycloalkyl by itself or a moiety of cycloalkoxy is e.g. cyclopropyl, cyclobutyl, cyclopentyl, cyclohexyl or cycloheptyl. Haloalkyl is a mono- to perhalogenated alkyl radical, e.g. $CH_2I$, $CH_2Br$, $CH_2Cl$, $CH_2F$, $CHCl_2$, $CCl_3$, $CBr_3$, $CF_3$, $C_2F_5$, $CFClBr$ etc., which radical may also be substituted simultaneously by different halogen atoms; the $CF_3$ radical is preferred. Typical representatives of 5-membered heterocyclic ring systems are: furan, thiophene, pyrrole, isoxazole, isothiazole, furazan, imidazole, 1,2,4-triazole, 1,2,3-triazole, pyrazole, pyrroline, oxazole, thiazole, thiadiazoles, pyrazoline, thiazoline, pyrazolidine, pyrrolidine, oxazolidine, thiazolidine, oxadiazole, imidazoline, imidazolidine, tetrahydrofuran; and typical representatives of 6-membered heterocyclic ring systems are: pyridine, pyridazine, pyrimidine, pyrazine, thiazine, thiadiazines, pyrans, piperidine, piperazine, morpholine, perhydrothiazine, dioxane and the partially hydrogenated or partially saturated homologs thereof, etc. Throughout this specification, oxo-substituted heterocyclic systems are in particular 5- and 6-membered lactones and lactams, e.g. butyrolactones, valerolactones, butyrolactam, valerolactam, and also bicyclic systems such as camphane.

The parent substances (OH group in the 5-position) on which the compounds of formula I are based are known from U.S. Pat. No. 4,468,390. Milbemycin D hemiesters, the 5-OH group of which is esterified with a dibasic acid, are described in European patent specification No. 102 721. Furthermore, milbemycin carbonates (oxycarbonyloxy group in the 5-position) are known from European patent specification No. 142 969. These prior art compounds display distinct weaknesses (q.v. the biological tests described later) when used for controlling endoparasitic worms in warm-blooded animals.

Within the scope of formula I, the following subgroups are interesting:
(a) compounds of formula I, wherein
R is methyl, ethyl, isopropyl or sec-butyl;
$R_1$ is hydrogen, fluorine or methyl;
$R_2$ is one of the groups

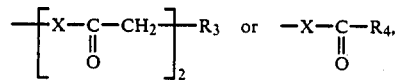

in which formulae
X is oxygen or sulfur;
$R_3$ is halogen; and
$R_4$ is hydrogen, $C_1$–$C_4$alkoxy, $C_3$–$C_6$cycloalkoxy or $C_2$–$C_6$-alkenyloxy; or $C_1$–$C_6$alkyl which is unsubstituted or substituted by halogen, $C_1$–$C_4$alkoxy, hydroxy and/or COOG, G being hydrogen or an alkali metal cation; or $R_4$ is $C_3$-$C_6$cycloalkyl; $C_2$-$C_6$alkenyl which is unsubstituted or substituted by halogen; $C_2$-$C_6$alkynyl which is unsubstituted or substituted by halogen; or phenyl which is unsubstituted or substituted by halogen, methyl, methoxy, nitro, cyano and/or $CF_3$.

Within subgroup (a), the following subgroup is to be singled out for special mention:

(b) Compounds of formula I, wherein
R and $R_1$ are as defined under (a);
$R_2$ is one of the groups

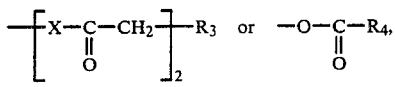

in which formulae
X is oxygen or sulfur;
$R_3$ is fluorine or chlorine; and
$R_4$ is $C_1$-$C_4$alkoxy, $C_3$-$C_6$cycloalkoxy or $C_2$-$C_6$alkenyloxy; or $C_1$-$C_6$alkyl which is unsubstituted or substituted by fluorine, chlorine, $C_1$-$C_4$alkoxy, hydroxy or COOH; $C_3$-$C_6$cycloalkyl; $C_2$-$C_6$-alkenyl which is unsubstituted or substituted by fluorine or chlorine; $C_2$-$C_6$alkynyl which is unsubstituted or substituted by fluorine or chlorine; or phenyl which is unsubstituted or substituted by fluorine, chlorine, methyl, methoxy, nitro, cyano and/or $CF_3$.

Also to be singled out are:
(c) compounds of formula I, wherein
R and $R_1$ are as defined in subgroup (a);
$R_2$ is the group

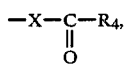

wherein
X is oxygen or sulfur; and
$R_4$ is a 5- or 6-membered unsaturated or saturated heterocyclic ring system which contains one to three hetero atoms selected from the series consisting of nitrogen, oxygen and sulfur and which is unsubstituted or substituted by oxo and/or by one to three substituents selected from halogen, $C_1$-$C_4$alkyl, $C_1$-$C_4$alkoxy and/or $C_1$-$C_4$haloalkyl.

Preferred compounds within subgroup (c) are:
(d) compounds of formula I, wherein
R and $R_1$ are as defined in subgroup (a);
$R_2$ is the group

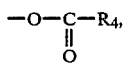

wherein
$R_4$ is a 5- or 6-membered unsaturated or saturated heterocyclic ring system which contains one to three hetero atoms selected from the series consisting of nitrogen, oxygen and sulfur and which is unsubstituted or substituted by oxo and/or by one to three substituents selected from halogen, $C_1$-$C_4$alkyl, $C_1$-$C_4$alkoxy and/or $C_1$-$C_4$haloalkyl, said heterocyclic ring system being selected from the group consisting of furan, thiophene, pyrrole, isoxazole, isothiazole, furazan, imidazole, 1,2,4-triazole, 1,2,3-triazole, pyrazole, pyrroline, oxazole, thiazole, thiadiazoles, pyrazoline, thiazoline, pyrazolidine, pyrrolidine, oxazolidine, thiazolidine, oxadiazole, imidazoline, imidazolidine, tetrahydrofuran; pyridine, pyridazine, pyrimidine, pyrazine, thiazine, thiadiazines, pyrans, piperidine, piperazine, morpholine, perhydrothiazine, dioxane and the partially hydrogenated or partially saturated homologs thereof, butyrolactones, valerolactones, butyrolactam, valerolactam, or camphane.

Preferred individual substances of formula I are:
5-O-acetoxyacetylmilbemycin D
5-O-acetoxyacetylmilbemycin $A_4$
5-O-acetoxyacetylmilbemycin $A_3$
5-O-acetoxyacetyl-13-deoxy-22,23-dihydroavermectin-Bla-aglycone
5-O-(3,4-dihydro-2H-pyran-2-yl)carboxyacetylmilbemycin D
5-O-(3,4-dihydro-2H-pyran-2-yl)carboxyacetylmilbemycin $A_4$
5-O-(3,4-dihydro-2H-pyran-2-yl)carboxyacetylmilbemycin $A_3$
5-O-(5-pyrrolidon-2-yl)carboxyacetylmilbemycin D
5-O-(5-pyrrolidon-2-yl)carboxyacetylmilbemycin $A_4$
5-O-((S)-5-pyrrolidon-2-yl)carboxyacetylmilbemycin $A_4$
5-O-((R)-5-pyrrolidon-2-yl)carboxyacetylmilbemycin $A_4$
5-O-camphanoyloxyacetylmilbemycin $A_4$
5-O-((S)-2-hydroxypropionyloxy)acetylmilbemycin D
5-O-chloroacetoxyacetylmilbemycin D
5-O-chloroacetoxyacetoxyacetylmilbemycin D
5-O-chloroacetoxyacetoxyacetoxyacetylmilbemycin D
5-O-acetylthioacetylmilbemycin D
5-O-fluoroacetoxyacetylmilbemycin $A_4$
5-O-formyloxyacetylmilbemycin $A_4$
5-O-benzoyloxyacetylmilbemycin $A_4$
5-O-propionyloxyacetylmilbemycin $A_4$
5-O-methoxyacetoxyacetylmilbemycin $A_4$
5-O-(acetoxy)fluoroacetylmilbemycin $A_4$
5-O-(2-acetoxy)propionylmilbemycin $A_4$
5-O-(2-acetoxy)butanoylmilbemycin $A_4$
5-O-cyclopropylcarbonyloxyacetylmilbemycin $A_4$
5-O-methoxycarbonyloxyacetylmilbemycin $A_4$
5-O-(3-chlorobenzoyloxy)acetylmilbemycin D
5-O-(3-chlorobenzoyloxy)acetylmilbemycin $A_4$
5-O-(3-chlorobenzoyloxy)acetylmilbemycin $A_3$ and
5-O-((S)-2-hydroxypropionyloxy)acetylmilbemycin $A_4$.

The present invention relates not only to the compounds of formula I, but also to the novel process for the preparation thereof.

Compounds of formula II below are known from the literature as milbemycins:

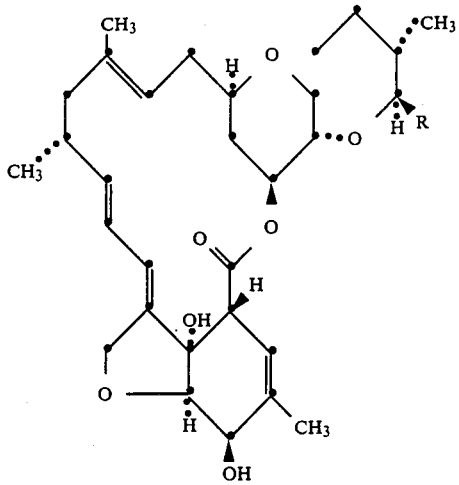

| R = CH₃ | milbemycin A₃ from U.S. Pat. No. 3 950 360 |
|---|---|
| R = C₂H₅ | milbemycin A₄ from U.S. Pat. No. 3 950 360 |
| R = isoC₃H₇ | milbemycin D from U.S. Pat. No. 4 346 171 |
| R = sec-C₄H₉ | 13-deoxy-22,23-dihydro-C-076-B1a-aglycone, or 13-deoxy-22,23-dihydroavermectin-B1a-aglycone from U.S. Pat. No. 4 173 571. |

Throughout this specification, compounds wherein R is sec-butyl shall also be considered as belonging to the category of milbemycin derivatives, although they are derived from avermectin derivatives according to conventional classification. Avermectin aglycones (carrying an OH group in position 13) can, however, be converted into milbemycin homologs in accordance with U.S. Pat. No. 4,173,571.

In accordance with the present invention, the compounds of formula I are prepared as follows:

A:

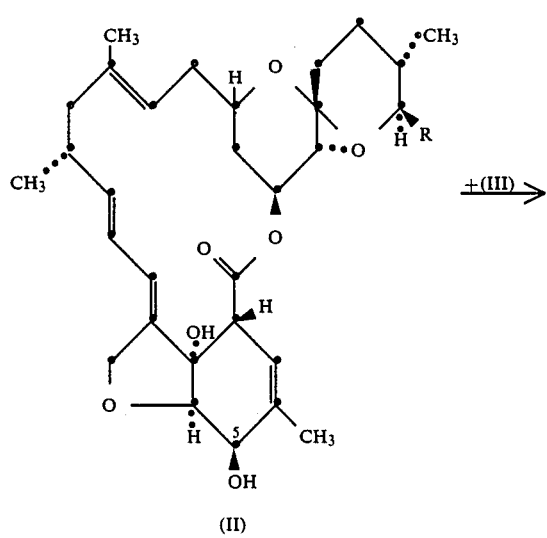

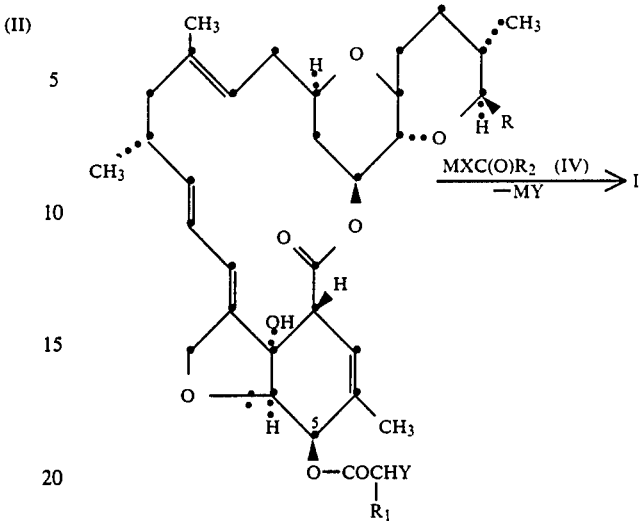

by converting the milbemycin derivative of formula II at the 5-OH group into an intermediate of formula V by esterification with a reactive acid derivative of formula III $$Y-CH-CO-Z \quad\quad (III)$$
$$|$$
$$R_1$$

and converting the compound of formula V into the final product of formula I by reaction with an alkali metal salt of a (thiolic) acid of formula IV, R, $R_1$, $R_2$ and X being as defined for formula I and M being an alkali metal cation selected from the series consisting of Li, Na and K, with Na or K being preferred. Suitable reactive acid derivatives are compounds capable of acetylation such as appropriately substituted acetyl halides or acetic anhydrides or the substituted acetic acid itself, all of which introduce the radical $$Y-CH-CO-$$
$$|$$
$$R_1$$

in the 5-position. Thus Z is halogen, preferably chlorine or bromine, —OH or the half oxygen function in the acid anhydride. Y is halogen, preferably chlorine, bromine or iodine, or azido or another leeving group which may be readily replaced by nucleophilic exchange, e.g. a sulfonic acid radical, preferably mesylate or tosylate. Preferred compounds of formula III are chloroacetyl chloride, bromoacetyl bromide, azidoacetyl chloride, chloroacetic anhydride, 2-mesylacetyl chloride. If the compound of formula III is an acid halide or acid anhydride, the reaction is preferably carried out in an inert solvent that does not include OH groups and in the presence of an organic base, e.g. pyridine, 4-dimethylaminopyridine, lutidine, collidine, trialkylamine, N-dialkylaniline, or a bicyclic non-nucleophilic base, e.g. 1,4-diazabicyclo[2.2.2]octane (DABCO), 1,5-diazabicyclo[4.3.0]non-5-ene (DBN) or 1,8-diazabicyclo[5.4.0]undec-7-ene (1.5-5) (DBU). The reaction is generally carried out in the temperature range from −30° to +70° C., preferably from −10° to +50° C. It is convenient to carry out the reaction in the presence of an inert solvent or mixture of solvents. Suitable solvents are e.g. aliphatic and aromatic hydrocarbons such as benzene, toluene, xylenes, petroleum ether, hexane; halogenated hydrocarbons such as chlorobenzene, methylene chloride, ethylene chloride, chloroform, carbon tetrachloride, tetrachloroethylene; ethers and etheral compounds such as dialkyl ethers (diethyl ether, diisopropyl ether, tert-butylmethyl ether etc.), anisole, dioxane, tetrahydrofuran; nitriles such as acetonitrile, propionitrile, esters such as ethyl acetate, propyl acetate or butyl acetate; ketones such as acetone diethyl ketone, methyl ethyl ketone; compounds such as dimethyl sulfoxide (DMSO), dimethylformamide (DMF) and mixtures of such solvents with one another. The reaction may also be carried out in an excess of one of the above bases.

If the compound of formula III is a carboxylic acid (Z=OH), then the reaction to esterify the compound of formula II with a compound of formula III is advantageously carried out in the presence of a condensing agent customarily employed in esterification reactions, e.g in the presence of a carbodiimide [dicyclohexyldiimide (DDC)] or of a 1-alkyl-2-halopyridinium salt [1-methyl-2-chloropyridinium iodide]. This reaction is preferably carried out in one of the above inert solvents and in the temperature range from $-30°$ to $+70°$ C., preferably from $-10°$ to $+50°$ C. It is preferred to carry out the esterification reaction in the presence of a base, for example in the presence of an organic amine, e.g. a trialkylamine (trimethylamine, triethylamine, tripropylamine, diisopropylethylamine etc.), a pyridine (pyridine itself, 4-dimethylaminopyridine, 4-pyrrolidylaminopyridine etc.), a morpholine (N-methylmorpholine), an N,N-dialkylaniline (N,N-dimethylaniline, N-methyl-N-ethylaniline) etc.

The reaction to convert the compound of formula V into a compound of formula I may be carried out in the presence of one of the above bases and/or of a catalyst. Further suitable bases are an excess of the alkali metal salt of formula IV, or an inorganic base such as an alkali metal carbonate, alkaline earth metal carbonate, alkali metal bicarbonate or alkaline earth metal bicarbonate, e.g. $Na_2CO_3$, $K_2CO_3$, $MgCO_3$, $NaHCO_3$, $KHCO_3$ etc. Suitable catalysts are alkali metal iodides, in particular NaI or KI. This reaction is preferably carried out in an aprotic polar solvent such as dimethyl sulfoxide, dimethylformamide, dimethylacetamide, acetonitrile, benzonitrile or hexamethylphosphoric triamide. Suitable reaction temperatures are in the range from $\pm 0°$ to $+150°$ C., preferably from $+20°$ to $+120°$ C.

The compounds of formula I may also be prepared by a modified reaction in accordance with variant B: by converting a milbemycin derivative of formula II at the 5-OH group direct into the final product of formula I by esterification with a reactive acid derivative of formula VI

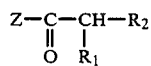

(VI)

wherein Z is as defined for formula III. The reaction conditions stated for the reaction II+III→V also apply to this esterification reaction.

Whereas variant B is a direct esterification, variant A is merely the same reaction carried out in two partial steps.

The compounds of formula VI are known or they can be prepared by methods analogous to those for preparing known representatives, e.g. in accordance with the following scheme:

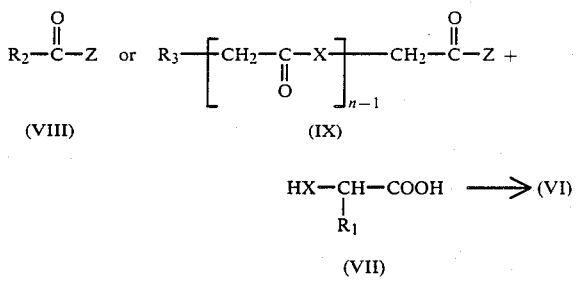

in which formulae the substituents are as defined above. In said reaction, e.g. an acid of formula VII (such as glycolic acid, lactic acid or thioglycolic acid) is converted, under the conditions stated above, into a compound of formula VI, wherein Z is OH, by esterification with a reactive acid derivative of formula VIII or IX. The acid of formula VI (Z=OH) obtained in this manner may either be used direct for the conversion of the compound of formula II into a compound of formula I or it may be first converted into one of its reactive acid derivatives (e.g. its acid chloride) of formula VI by a conventional method, e.g. conversion of the acid into the acid chloride by reaction with thionyl chloride. Particularly preferred reactive acid derivatives of formula VI are those wherein Z is halogen, preferably chlorine or bromine or the half acid function (forming an anhydride). Typical representatives of formula VI are:
O-acetylglycoloyl bromide
2-acetyloxyacetyl chloride
O-propionylglycolic acid and the chloride and the bromide thereof
2-thioacetylacetic acid and the chloride and the bromide thereof
2-acetoxypropionyl chloride
dichloroacetylglycoloyl chloride
trifluoroacetylglycoloyl chloride
2-benzoyloxyacetyl chloride The compounds of formulae III, IV, VII, VIII and IX are generally known or they can be prepared by methods analogous to those for preparing their known representatives.

The described process for the preparation of compounds of formula I constitutes in all its partial steps an object of the present invention.

The compounds of formula I are most suitable for controlling pests of animals and plants, including ectoparasites of animals. These last mentioned pests comprise those of the order Acarina, in particular pests of the families Ixodidae, Dermanyssidae, Sarcoptidae, Psoroptidae; of the orders Mallophaga, Siphonaptera, Anoplura (e.g. family of the Haematopinidae); and of the order Diptera, in particular pests of the families Muscidae, Calliphoridae, Oestridae, Tabanidae, Hippoboscidae, and Gastrophilidae.

The compounds of formula I can also be used against hygiene pests, especially of the order Diptera (families Sarcophagidae, Anophilidae and Culicidae); of the order Orthoptera, of the order Dictyoptera (e.g. family of the Blattidae), and of the order Hymenoptera (e.g. family of the Formicidae).

The compounds of formula I also have a lasting action against mites and insects which are parasites of plants. When used to control spider mites of the order Acarina, they are effective against eggs, nymphs and adults of Tetranychidae (Tetranychus spp. and Panonychus spp.) They also have excellent activity against sucking insects of the order Homoptera, in particular against pests of the families Aphididae, Delphacidae, Cicadellidae, Psyllidae, Coccidae, Diaspididae and Eriophydidae (e.g. the rust mite on citrus fruit); of the orders Hemiptera, Heteroptera and Thysanoptera; and against plant-feeding insects of the orders Lepidoptera, Coleoptera, Diptera and Orthoptera.

The compounds of formula I are also suitable for use against soil pests.

The compounds of formula I are therefore effective against all development stages of sucking and feeding insects in crops such as cereals, cotton, rice, maize, soybeans, potatoes, vegetables, fruit, tobacco, hops, citrus fruit, avocados and others.

The compounds of formula I are also effective against plant nematodes of the species Meloidogyne, Heterodera, Pratylenchus, Ditylenchus, Radolphus, Rhizoglyphus and others.

Furthermore, the compounds of formula I act against helminths, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesphagostomum, Charbertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formula I is their activity against those parasites which are resistant to benzimidazole-based parasiticides.

Certain species of the genera Nematodirus, Cooperia and Oesophagostomum attack the intestinal tract of the host animal, whereas others of the species Haemonchus and Ostertagia parasiticise in the stomach and those of the species Dictyocaulus in the lung tissue. Parasites of the families Filariidae and Setariidae are found in internal cell tissue and internal organs, e.g. in the heart, blood vessels, lymph vessels and in subcutaneous tissue. In this connection, particular mention is to be made of the dog heartworm, Dirofilaria immitis. The compounds of formula I are highly effective against these parasites.

The compounds of formula I are also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compounds of this invention are also effective against parasites of the species Wuchereria, Brugia, Onchocerca and Loa of the family of the Filariidae which occur in the blood, in tissue and various organs, and, in addition, against Dracunculus and parasites of the species Strongyloides and Trichinella which infest in particular the gastro-intestinal tract.

The compounds of formula I are used in unmodified form or, preferably, together with the adjuvants conventionally employed in the art of formulation, and are therefore formulated in known manner e.g. to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 10 mg/kg of body weight, and are applied to enclosed crop areas, to pens, livestock buildings or other buildings in amounts of 10 g to 1000 g per hectare.

The formulations, i.e. the compositions, preparations or mixtures containing the compound of formula I (active ingredient) are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredient to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholiphids.

The surfactants customarily employed in the art of formulation are described e.g. in "McCutcheon's Detergents and Emulsifiers Annual", MC Publishing Corp., Ridgewood, N.J., 1982.

The pesticidal compositions usually contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1-10,000 ppm of active ingredient.

The present invention therefore also relates to pesticidal compositions which contain as active ingredient at least one compound of formula I, together with customary carriers and/or dispersing agents.

The compositions may also contain further ingredients such as stabilisers, antifoams, viscosity regulators, binders, tackifiers as well as fertilisers or other active ingredients for obtaining special effects.

PREPARATORY EXAMPLES (α) Preparation of intermediates of formula V

α1. Preparation of 5-O-chloroacetylmilbemycin D

While cooling with ice (0°–5° C.), 168 mg of chloroacetyl chloride are slowly added dropwise with an injection syringe to a solution of 400 mg of milbemycin D in 10 ml of pyridine. The cloudy yellowish reaction solution is poured at 0° C. into 100 ml of ice-cold 1N aqueous hydrochloric acid and extracted with four 20 ml portions of diethyl ether (ether). The carefully washed and dried ether solution is concentrated in vacuo, affording an amorphous foamy product which is purified by chromatography through silica gel (elution with a 98:2 mixture of methylene chloride/methanol), affording 410 mg of colourless amorphous final product.

$^1$H-NMR (300 MHz; CDCl; TMS=tetramethylsilane) 5.32 (s) (—CH$_2$—Cl), 3.25 (narrow multiplet) (C$_2$H; i.e. H-signal in position 2); mass spectrum m/e: 632 (M$^+$; C$_{35}$H$_{49}$ClO$_8$).

α2. Preparation of 5-O-chloroacetylmilbemycin A$_4$ and of 5-O-chloroacetylmilbemycin A$_3$ Following the procedure of Example α1, 1.72 g of 5-O-chloroacetylmilbemycin A$_4$ and 0.77 g of 5-O-chloroacetylmilbemycin A$_3$ are obtained from 3.00 g of a mixture of 70% of milbemycin A$_4$ and 30% of milbemycin A$_3$ with 0.88 ml of chloroacetyl chloride and 4.4 ml of pyridine in 25 ml of methylene chloride after chromatographic separation through silica gel (elution with a 2:1 mixture of n-hexane and diethyl ether).

NMR data: 5-O-Chloroacetylmilbemycin A$_4$.

$^1$H-NMR (250 MHz, CDCl$_3$): 3.06 ppm (dt, J$_d$=2, J$_t$=8 Hz) (C$_{25}$H); 4.11 ppm (d, J=7) (C$_6$H); 4.18 ppm (s) (—CH$_2$Cl); 5.57 ppm (bd, J=7) (C$_5$H); 5-O-Chloroacetylmilbemycin A$_3$.

$^1$H-NMR (250 MHz, CDCl$_3$): 3.26 ppm (m) (C$_{25}$H); 4.10 ppm (d, J=7) (C$_6$H); 4.16 ppm (s) (—CH$_2$Cl); 5.58 ppm (d, J=7) (C$_5$H).

α3. Preparation of 5-O-bromoacetylmilbemycin A$_4$

Following the procedure of Example α1, 5-O-bromoacetylmilbemycin A$_4$ is obtained as an amorphous solid product from milbemycin A$_4$ (R═C$_2$H$_5$) and bromoacetyl bromide in pyridine.

α4. Preparation of 5-O-iodoacetylmilbemycin D 150 mg of 5-O-chloroacetylmilbemycin D and 50 mg of potassium iodide are dissolved in 10 ml of acetone and the solution is stirred for 24 hours at room temperature. The reaction mixture is diluted with the 5-fold amount of water and then extracted with four 10 ml portions of diethyl ether. The crude product obtained from the ether solution is chromatographed through silica gel (q.v. Example α1), affording 80 mg of pure product (m.p. 133°–137° C.).

α5. Preparation of 5-O-azidoacetylmilbemycin D

Following the procedure of Example α4, 92 mg of 5-O-azidoacetylmilbemycin D are obtained from 150 mg of 5-O-chloroacetylmilbemycin D and 35 mg of sodium azide (NaN$_3$).

α6. Preparation of 5-O-(2-chloro)butanoylmilbemycin D 1.5 ml of pyridine and 212 mg of N,N-dicyclohexylcarbodiimide are added to a solution of 284 mg of milbemycin D and 156 mg of 2-chlorobutyric acid in 3 ml of tetrahydrofuran. The reaction mixture is stirred for 12 hours at room temperature and then poured into 50 ml of ice-cold 1N aqueous hydrochloric acid and extracted with two 50 ml portions of diethyl ether. The ether phases are washed with 30 ml of saturated, aqueous NaHCO$_3$ solution and then with 30 ml of saturated, aqueous NaCl solution, dried over MgSO$_4$ and filtered. The filtrate is concentrated by evaporation and the resultant crude product is chromatographed through silica gel (elution with a 7:1 mixture of hexane and ethyl acetate), affording 282 mg of 5-O-(2-chloro)butanoylmilbemycin D.

$^1$H-NMR (250 MHz, CDCl$_3$): 3.08 ppm (bd, J=9) (C$_{25}$H); 4.33 ppm (m) (OC(O)CH(Cl)CH$_2$); 5.55 ppm (d, J=6) (C$_5$H).

α7. Preparation of 5-O-bromofluoroacetylmilbemycin A$_4$

Over 30 minutes, 8 ml of a 0.25M solution of bromofluoroacetyl chloride in benzene is added dropwise at 0° C. to a solution of 542 mg of milbemycin A$_4$, 79 μl of pyridine and 6 mg of dimethylaminopyridine in 4 ml of methylene chloride. The reaction mixture is stirred for 30 minutes at 0° C. and for 3 hours at 25° C. and subsequently worked up. Chromatography of the crude product through silica gel (elution with a mixture of hexane and ethyl acetate) affords 662 mg of 5-O-bromofluoroacetylmilbemycin A$_4$.

Mass spectrum: m/e 680, 682 (M$^+$, C$_{34}$H$_{46}$BRFO$_8$)

The following intermediates of formula V can also be prepared in accordance with the foregoing Examples:

| No. | |
|---|---|
| α8. | 5-O—bromoacetylmilbemycin A₃ |
| α9. | 5-O—bromoacetylmilbemycin D |
| α10. | 5-O—chloroacetylmilbemycin A₄ |
| α11. | 5-O—fluoroacetylmilbemycin D |
| α12. | 5-O—methylsulfonyloxyacetylmilbemycin D |
| α13. | 5-O—p-tosyloxyacetylmilbemycin D |
| α14. | 5-O—azidoacetylmilbemycin A₃ |
| α15. | 5-O—azidoacetylmilbemycin A₄ |
| α16. | 5-O—ethylsulfonyloxyacetylmilbemycin A₄ |
| α17. | 5-O—chloroacetyl-13-deoxy-22,23-dihydroavermectin-B1a-aglycone |
| α18. | 5-O—bromoacetyl-13-deoxy-22,23-dihydroavermectin-B1a-aglycone |
| α19. | 5-O—azidoacetyl-13-deoxy-22,23-dihydroavermectin-B1a-aglycone | as well as the following compounds of formula V:

| Comp. No. | R | R₁ | Y |
|---|---|---|---|
| α20 | CH₃ | CH₃ | Cl |
| α21 | CH₃ | C₂H₅ | Cl |
| α22 | CH₃ | H | Cl |
| α23 | CH₃ | H | OSO₂C₆H₄CH₃(4) |
| α24 | C₂H₅ | H | OSO₂C₆H₄CH₃(4) |
| α25 | C₂H₅ | CH₃ | Cl |
| α26 | C₂H₅ | H | OSO₂CH₃ |
| α27 | C₂H₅ | C₃H₇-n | OSO₂C₆H₄CH₃(4) |
| α28 | C₂H₅ | C₂H₅ | OSO₂C₆H₄CH₃(4) |
| α29 | C₂H₅ | H | I |
| α30 | C₂H₅ | CH₃ | Br |
| α31 | C₃H₇-i | CH₃ | OSO₂C₆H₄CH₃(4) |
| α32 | C₃H₇-i | H | OSO₂CH₃ |
| α33 | C₄H₉-s | H | OSO₂CH₃ |
| α34 | C₄H₉-s | H | OSO₂C₆H₄CH₃(4) |
| α35 | C₄H₉-s | C₂H₅ | Cl |
| α36 | C₂H₅ | F | Br |
| α37 | C₂H₅ | H | OSO₂C₆H₄CH₃(4) |
| α38 | C₂H₅ | CH₃ | Br |
| α39 | C₂H₅ | H | OSO₂CH₃ |

(β) Preparation of compounds of formula I

β1. Preparation of 5-O-acetoxyacetylmilbemycin D

A solution of 150 mg of 5-O-chloroacetylmilbemycin D, 39 mg of sodium acetate and 2 mg of sodium iodide in 3 ml of dimethylformamide is stirred for 4 hours at 50° C. and then for 30 minutes at 90° C. under an atmosphere of argon and then poured into 50 ml of diethyl ether. The resultant solution is washed with 20 ml of water and then with 20 ml of saturated NaCl solution, dried over MgSO₄ and filtered. The filtrate is concentrated by evaporation and the resultant crude product is chromatographed through silica gel (elution with a 2:1 mixture of hexane and ethyl acetate), affording 100 mg of 5-O-acetoxyacetylmilbemycin D.

¹H-NMR (250 MHz, CDCl₃): 2.18 ppm (s) (CH₃C(O)O); 3.08 ppm (bd, J=10) (C₂₅H); 4.08 ppm (d, J=7) (C₆H); 4.69 ppm (d, J=15) (OC(O)CHHO); 4.77 ppm (d, J=15) (OC(O)CHHO); 5.61 ppm (d, J=7) (C₅H).

β2. Preparation of 5-O-acetoxyacetylmilbemycin A₄

(a) Following the procedure of Example β1, 78 mg of 5-O-acetoxyacetylmilbemycin A₄ are obtained from 150 mg of 5-O-chloroacetylmilbemycin A₄, 30 mg of sodium acetate and 2 mg of sodium iodide in 3 ml of dimethylformamide after chromatography through silica gel (elution with a 2:1 mixture of hexane and ethyl acetate).

(b) Over 10 minutes, 2 ml of a 0.09M solution of acetoxyacetyl chloride in benzene are added at 0° C. to a solution of 50 mg of milbemycin A₄, 73 μl of pyridine and 1 mg of dimethylaminopyridine in 1 ml of methylene chloride. The reaction mixture is stirred for 2 hours at 0° C. and then worked up. Chromatography of the crude product in accordance with the procedure of (a) affords 48 mg of product.

¹H-NMR (250 MHz, CDCl₃): 2.18 ppm (s) (CH₃OCO); 3.06 ppm (dt, J$_d$=2, J$_t$=8) (C₂₅H); 4.08 ppm (d, J=5) (C₆H); 4.66 ppm (d, J=15) (OC(O)CHHO); 4.75 ppm (d, J=15) (OC(O)CHHO); 5.61 ppm (bd, J=5) (C₅H).

β3. Preparation of 5-O-acetoxyacetylmilbemycin A₃

By following the procedure of Example β1, 53 mg of 5-O-acetoxyacetylmilbemycin A₃ are obtained from 100 mg of 5-O-chloroacetylmilbemycin A₃, 20 mg of sodium acetate and 2 mg of sodium iodide in 3 ml of dimethylformamide after chromatography through silica gel (elution with a 2:1 mixture of hexane and ethyl acetate).

¹H-NMR (250 MHz, CDCl₃): 3.27 ppm (m) (C₂₅H); 4.06 ppm (d, J=6) (C₆H); 4.68 ppm (d, J=15) (OC(O)CHHO); 4.76 ppm (d, J=15) (OC(O)CHHO); 5.61 ppm (d, J=6) (C₅H).

β4. Preparation of 5-O-(3,4-dihydro-2H-pyran-2-yl)carboxyacetylmilbemycin D

A solution of 150 mg of 5-O-chloroacetylmilbemycin D, 73 mg of sodium (±)-3,4-dihydro-2H-pyran-2-carboxylate and 2 mg of potassium iodide in 3 ml of dimethylformamide is stirred for 12 hours at 90° C. under an atmosphere of argon and subsequently diluted with 50 ml of diethyl ether. The resultant solution is washed with 20 ml of water and then with 20 ml of saturated NaCl solution, dried over MgSO₄ and filtered. The filtrate is concentrated by evaporation and the resultant crude product is chromatographed through silica gel (elution with a 6:1 mixture if hexane and ethyl acetate), affording 58 mg of 5-O-(3,4-dihydro-2H-pyran-2-yl)carboxyacetylmilbemycin D.

¹H-NMR (250 MHz, CDCl₃): 3.07 ppm (bd, J=10) (C₂₅H); 4.04 ppm and 4.06 ppm (2d, each J=7) (C₆H); 4.58 ppm (bd, J=15) (C₂₇HH); 4.66 ppm (bd, J=15) (C₂₇HH); 6.43 ppm (d, J=7) (O-CH=CH).

β5. Preparation of 5-O-(3,4-dihydro-2H-pyran-2-yl)carboxyacetylmilbemycin A₄

By following the procedure of Example β4, a solution of 150 mg of 5-O-chloroacetylmilbemycin A₄, 55 mg of sodium (±)-3,4-dihydro-2H-pyran-2-carboxylate and 2 mg of potassium iodide in 3 ml of dimethylformamide is reacted for 3 hours at 60° C. and for 1 hour at 80° C. Chromatography through silica gel (elution with a 4:1 mixture of hexane and ethyl acetate) affords 131 mg of 5-O-(3,4-dihydro-2H-pyran-2-yl)carboxyacetylmilbemycin A₄.

¹H-NMR (250 MHz, CDCl₃): 3.07 (bt, J=8) (C₂₅H); 4.06 ppm and 4.07 ppm (2d, each J=7) (C₆H); 4.58 ppm (bd, J=15) (C₂₇HH); 4.66 ppm (bd, J=15) (C₂₇HH); 6.44 ppm (d, J=7) (O-CH=CH).

β6. Preparation of 5-O-(3,4-dihydro-2H-pyran-2-yl)carboxyacetylmilbemycin A₃

By following the procedure of Example β4, 58 mg of 5-O-(3,4-dihydro-2H-pyran-2-yl)carboxyacetylmilbemycin A₃ are obtained from 80 mg of 5-O-chloroacetylmilbemycin A₃.

$^1$H-NMR (250 MHz, CDCl$_3$): 3.26 ppm (m) ($C_{25}H$); 4.05 ppm and 4.06 ppm (2d, each J=7) ($C_6H$); 4.58 ppm (bd, J=15) ($C_{27}HH$); 4.66 ppm (bd, J=15) ($C_{27}HH$); 6.46 ppm (d, J=7) (O-CH=CH).

β7. Preparation of 5-O-(5-pyrrolidon-2-yl)carboxyacetylmilbemycin D

A solution of 150 mg of 5-O-chloroacetylmilbemycin D, 107 mg of sodium DL-pyroglutamate and 2 mg of NaI in 3 ml of dimethylformamide is stirred for 4 hours at 70° C. under an atmosphere of argon and then diluted with 50 ml of diethyl ether. The resultant solution is washed with 20 ml of water and then with 20 ml of saturated NaCl solution, dried over MgSO$_4$ and filtered. The filtrate is concentrated and the crude product is chromatographed through silica gel (elution with ethyl acetate), affording 117 mg of 5-O-(5-pyrrolidon-2-yl)carboxyacetylmilbemycin D.

$^1$H-NMR (250 MHz, CDCl$_3$): 3.01 ppm (bd, J=10) ($C_{25}H$); 3.98 ppm (d, J=7) ($C_6H$); 5.56 ppm (bd, J=6) ($C_5H$).

β8. Preparation of 5-O-(5-pyrrolidon-2-yl)carboxyacetylmilbemycin A₄

By following the procedure of Example β7, 141 mg of 5-O-(5-pyrrolidon-2-yl)carboxyacetylmilbemycin A₄ are obtained from 150 mg of 5-O-chloroacetylmilbemycin A₄.

$^1$H-NMR (250 MHz, CDCl$_3$): 3.07 ppm (bt, J=9) ($C_{25}H$); 4.03 ppm (d, J=6) ($C_6H$); 5.62 ppm (bd, J=7) ($C_5H$).

β9. Preparation of 5-O-((S)-5-pyrrolidon-2-yl)carboxyacetylmilbemycin A₄

By following the procedure of Example β7, 64 mg of 5-O-((S)-5-pyrrolidon-2-yl)carboxyacetylmilbemycin A₄ are obtained from 100 mg of 5-O-chloroacetylmilbemycin A₄, 73 mg of sodium L-pyroglutamate and 2 mg of sodium iodide in 3 ml of dimethylformamide after chromatography through silica gel (elution with ethyl acetate).

$^1$H-NMR (250 MHz, CDCl$_3$): 3.08 ppm (dt, J$_d$=3, J$_t$=9) ($C_{25}H$); 4.03 ppm (d, J=7) ($C_6H$); 4.50 ppm (bd, J=15) ($C_{27}HH$); 4.59 ppm (bd, J=15) ($C_{27}HH$); 4.76 ppm (d, J=16) (Oc(O)CHHO); 4.84 ppm (d, J=16) (OC(O)CHHO); 5.62 ppm (bd, J=7) ($C_5H$).

β10. Preparation of 5-O-((R)-5-pyrrolidon-2-yl)carboxyacetylmilbemycin A₄

By following the procedure of Example β7, 91 mg of 5-O-((R)-5-pyrrolidon-2-yl)carboxyacetylmilbemycin A₄ are obtained from 100 mg of 5-O-chloroacetylmilbemycin A₄, 73 mg of sodium D-pyroglutamate and 2 mg of sodium iodide in 3 ml of dimethylformamide after chromatography through silica gel (elution with ethyl acetate).

$^1$H-NMR (250 MHz, CDCl$_3$): 3.08 ppm (dt, J$_d$=3, J$_t$=9) ($C_{25}H$); 4.04 ppm (d, J=7) ($C_6H$); 4.59 ppm (bd, J=15) ($C_{27}HH$); 4.69 ppm (bd, J=15) ($C_{27}HH$); 4.76 ppm (d, J=15) (OC(O)CHHO); 4.84 ppm (d, J=15) (OC(O)CHHO); 5.63 ppm (d, J=7) ($C_5H$).

β11. Preparation of 5-O-camphanoyloxyacetylmilbemycin A₄

By following the procedure of Example β7, 85 mg of 5-O-camphanoyloxyacetylmilbemycin A₄ are obtained from 100 mg of 5-O-chloroacetylmilbemycin A₄, 107 mg of sodium (−)-camphanate and 2 mg of sodium iodide in 3 ml of dimethylformamide after chromatography through silica gel (elution with a 2:1 mixture of hexane and ethyl acetate).

$^1$H-NMR (250 MHz, CDCl$_3$): 3.08 ppm (dt, J$_d$=3, J$_t$=9) ($C_{25}H$); 4.06 ppm (d, J=7) ($C_6H$); 4.59 ppm (bd, J=15) ($C_{27}HH$); 4.68 ppm (bd, J=15) ($C_{27}HH$); 4.87 ppm (bs) (OC(O)CH$_2$O); 5.63 ppm (bd, J=7) ($C_5H$).

β12. Preparation of 5-O-((S)-2-hydroxypropionyloxy)acetylmilbemycin D

By following the procedure of Example β7, 77 mg of 5-O-((S)-2-hydroxypropionyloxy)acetylmilbemycin D are obtained from 100 mg of 5-O-chloroacetylmilbemycin D, 36 mg of sodium L-lactate and 2 μl of triethylamine in 3 ml of dimethylformamide after chromatography through silica gel (elution with a 2:1 mixture of hexane and ethyl acetate).

$^1$H-NMR (250 MHz, CDCl$_3$): 3.07 ppm (bd, J=10) ($C_{25}H$); 4.06 ppm (d, J=7) ($C_6H$); 4.78 ppm (d, J=15) (OC(O)CHHO); 4.86 ppm (d, J=15) (OC(O)CHHO); 5.60 ppm (bd, J=7) ($C_5H$).

β13. Preparation of 5-O-chloroacetoxyacetylmilbemycin D, 5-O-chloroacetoxyacetoxyacetylmilbemycin D and 5-O-chloroacetoxyacetoxyacetoxyacetylmilbemycin D A solution of 305 mg of chloroacetylmilbemycin D, 168 mg of sodium chloroacetate and 5 mg of sodium bicarbonate in 5 ml of acetone is reacted by following the procedure of Example β7. Chromatography through silica gel (elution with a 4:1 mixture of hexane and ethyl acetate) affords 45 mg of 5-O-chloroacetoxyacetylmilbemycin D.

$^1$H-NMR (250 MHz, CDCl$_3$): 3.08 ppm (bd, J=10) ($C_{25}H$); 4.07 ppm (d, J=7) ($C_6H$); 4.21 ppm (s) (—CH$_2$Cl); 4.78 ppm (d, J=16) (OC(O)CHHO); 4.86 ppm (d, J=16) (OC(O(CHHO)).

Elution with a 3:1 mixture of hexane and ethyl acetate affords 42 mg of 5-O-chloroacetoxyacetoxyacetylmilbemycin D $^1$H-NMR (250 MHz, CDCl$_3$): 3.08 ppm (bd, J=10) ($C_{25}H$); 4.07 ppm (d, J=7) ($C_6H$); 4.20 ppm (s) (—CH$_2$Cl); 4.77 ppm (d, J=15) ($C_5$—OC(O)CHHO); 4.84 ppm (d, J=15) ($C_5$—OC(O)CHHO); 4.85 ppm (s) (OC(O)CH$_2$O).

Elution with a 2:1 mixture of hexane and ethyl acetate affords 23 mg of 5-O-chloroacetoxyacetoxyacetoxyacetylmilbemycin D $^1$H-NMR (250 MHz, CDCl$_3$): 3.08 ppm (bd, J=10) ($C_{25}H$); 4.06 ppm (d, J=7) ($C_6H$); 4.21 ppm (s) (—CH$_2$Cl); 4.76 ppm (d, J=15) ($C_5$—OC(O)CHHO); 4.84 ppm (d, J=15) ($C_5$—*OC(O)CHHO*); 4.85 ppm (s) (2×OC(O)CH$_2$O).

β14. Preparation of 5-O-acetylthioacetylmilbemycin D

A solution of 150 mg of 5-O-chloroacetoxyacetylmilbemycin D, 54 mg of potassium thioacetate and 10 μl of pyridine in 3 ml of N,N-dimethylacetamide is stirred for 1 hour at 70° C. and then poured into 50 ml of diethyl ether. The resultant solution is washed with 20 ml of water and then with 20 ml of saturated NaCl solution, dried over MgSO₄ and filtered. The filtrate is concentrated by evaporation and the crude product is chromatographed through silica gel (elution with a 4:1 mixture of hexane and ethyl acetate), affording 121 mg of 5-O-acetylthioacetylmilbemycin D.

¹H-NMR (250 MHz, CDCl₃): 2.37 ppm (s) (CH₃(C(O)S); 3.08 ppm (d, J=10) (C₂₅H); 3.76 ppm (d, J=16) (OC(O)CHHO); 3.86 ppm (d, J=16) (OC(O)CHHO); 4.06 ppm (d, J=7) (C₆H).

β15. Preparation of 5-O-(acetoxy)fluoroacetylmilbemycin A₄

A solution of 150 mg of 5-O-bromofluoroacetylmilbemycin A₄, 27 mg of sodium acetate and 2 mg of sodium iodide in 2 ml of dimethylformamide is stirred for 1 hour at 25° C. and for 3½ hours at 50° C. and subsequently worked up. The crude product is chromatographed through silica gel (elution with a mixture of hexane and ethyl acetate), affording 61 mg of product.

Mass spectrum: m/e: 660 (M⁺, C₃₆H₄₉FO₁₀).

¹H-NMR (300 MHz, CDCl₃): 3.07 ppm (dt, J_d=2, J_t=9) (C₂₅H); 6.51 ppm (d, J=53) (OC(O)CHFO).

The compounds of formula I listed below can also be prepared by the procedures described. The recitation shall be understood as being exemplary and in no way limitative.

TABLE 1

Compounds of formula I (wherein R₁ = H)

| Comp. No. | R | R₂ | Physical data or reference to Example No. |
|---|---|---|---|
| 1.1 | CH₃ | OC(O)CH₃ | β3 |
| 1.2 | CH₃ | OC(O)-[cyclic structure with O] | β6 |
| 1.3 | CH₃ | OC(O)CH₂Cl | |
| 1.4 | CH₃ | OC(O)CH₂F | |
| 1.5 | C₂H₅ | OC(O)CH₃ | β2 |
| 1.6 | C₂H₅ | OC(O)CH₂F | m/e: 660(M⁺; C₃₆H₄₉FO₁₀) |
| 1.7 | C₂H₅ | OC(O)CH₂Cl | m/e: 676(M⁺; C₃₆H₄₉ClO₁₀) |
| 1.8 | C₂H₅ | OC(O)CCl₃ | m/e: 746(M⁺; C₃₆H₄₇Cl₃O₁₀) |
| 1.9 | C₂H₅ | OC(O)-C(CH₃)(H)(OH) | m/e: 672(M⁺; C₃₇H₅₂O₁₁) |
| 1.10 | C₂H₅ | OC(O)H | m/e: 628(M⁺; C₃₅H₄₈O₁₀) |
| 1.11 | C₂H₅ | OC(O)CH₂CH₃ | m/e: 656(M⁺; C₃₇H₅₂O₁₀) |
| 1.12 | C₂H₅ | OC(O)C₄H₉—t | m/e: 648(M⁺; C₃₉H₅₆O₁₀) |
| 1.13 | C₂H₅ | OC(O)C₃H₇—i | m/e: 670(M⁺; C₃₈H₅₄O₁₀) |
| 1.14 | C₂H₅ | OC(O)cyclopropyl | m/e: 668(M⁺; C₃₈H₅₂O₁₀) |
| 1.15 | C₂H₅ | OC(O)CH=CH₂ | m/e: 654(M⁺; C₃₇H₅₀O₁₀) |
| 1.16 | C₂H₅ | OC(O)C≡CH | m/e: 652(M⁺; C₃₇H₄₈O₁₀) |
| 1.17 | C₂H₅ | OC(O)CH₂CH₂COOH | m/e: 700(M⁺; C₃₈H₅₂O₁₂) |
| 1.18 | C₂H₅ | OC(O)OCH₃ | m/e: 658(M⁺; C₃₆H₅₀O₁₁) |
| 1.19 | C₂H₅ | OC(O)OCH=CH₂ | m/e: 670(M⁺; C₃₇H₅₀O₁₁) |
| 1.20 | C₂H₅ | OC(O)CH₂CH₂CH₂F | |
| 1.21 | C₂H₅ | OC(O)CH₂CH₂CH₂Cl | m/e: 704(M⁺; C₃₈H₅₃ClO₁₀) |
| 1.22 | C₂H₅ | OC(O)(CH₂)₇CH=CH(CH₂)₇CH₃ | |
| 1.23 | C₂H₅ | OC(O)C₆H₅ | m/e: 704(M⁺; C₄₁H₅₂O₁₀) |
| 1.24 | C₂H₅ | OC(O)-[cyclic structure with O, CH₃] | β11 |
| 1.25 | C₂H₅ | OC(O)C₆H₄(OH)(2) | m/e: 720(M⁺; C₄₁H₅₂O₁₁) |
| 1.26 | C₂H₅ | OC(O)C₆H₄Cl(3) | m/e: 738(M⁺; C₄₁H₅₁ClO₁₀) |
| 1.27 | C₂H₅ | OC(O)C₆H₄NO₂(4) | m/e: 749(M⁺; C₄₁H₅₁NO₁₂) |
| 1.28 | C₂H₅ | OC(O)-[cyclic structure with O] | β5 |

TABLE 1-continued

Compounds of formula I (wherein $R_1 = H$)

| Comp. No. | R | $R_2$ | Physical data or reference to Example No. |
|---|---|---|---|
| 1.29 | $C_2H_5$ | [structure: pyrrolidinone ring with OC(O)- and NH] | β8 |
| 1.30 | $C_2H_5$ | [structure: pyrrolidinone ring with OC(O)- and NH] | β10 |
| 1.31 | $C_2H_5$ | [structure: pyrrolidinone ring with OC(O)- and NH] | β9 |
| 1.32 | $C_2H_5$ | [structure: OC(O)-pyridinyl] | m/e: 705(M⁺; $C_{40}H_{51}NO_{10}$) |
| 1.33 | $C_2H_5$ | [structure: OC(O)-thienyl] | m/e: 710(M⁺; $C_{39}H_{50}O_{16}S$) |
| 1.34 | $C_3H_7$—i | $OC(O)CH_3$ | β1 |
| 1.35 | $C_3H_7$—i | $OC(O)CH_2Cl$ | β13 |
| 1.36 | $C_3H_7$—i | $OC(O)CH_2OC(O)CH_2Cl$ | β13 |
| 1.37 | $C_3H_7$—i | $OC(O)CH_2[OC(O)CH_2]_2Cl$ | β13 |
| 1.38 | $C_3H_7$—i | $OC(O)CH(OH)CH_3$ | β12 |
| 1.39 | $C_3H_7$—i | [structure: OC(O)-pyranyl] | β4 |
| 1.40 | $C_3H_7$—i | [structure: OC(O)-pyrrolidinone] | β7 |
| 1.41 | $C_3H_7$—i | $SC(O)CH_3$ | β14 |
| 1.42 | $C_4H_9$—s | $OC(O)CH_3$ | |
| 1.43 | $C_4H_9$—s | $OC(O)CH_2Cl$ | |
| 1.44 | $C_4H_9$—s | $OC(O)C_6H_4NO_2(3)$ | |
| 1.45 | $C_4H_9$—s | [structure: OC(O)-thienyl] | |
| 1.46 | $C_2H_5$ | $OC(O)(CH_2)_{16}CH_3$ | m/e: 866(M⁺; $C_{52}H_{82}O_{10}$) |
| 1.47 | $C_2H_5$ | $OC(O)C_6H_4F(2)$ | m/e: 722(M⁺; $C_{41}H_{51}FO_{10}$) |
| 1.48 | $C_2H_5$ | $OC(O)C_6H_3(NO_2)_2(3,5)$ | m/e: 794(M⁺; $C_{41}H_{50}N_2O_{14}$) |
| 1.49 | $C_2H_5$ | $OC(O)$—furan-2-yl | m/e: 694(M⁺; $C_{39}H_{50}O_{11}$) |

TABLE 1-continued

Compounds of formula I (wherein $R_1$ = H)

| Comp. No. | R | $R_2$ | Physical data or reference to Example No. |
|---|---|---|---|
| 1.50 | $C_2H_5$ | pyrazine-OC(O)- | m/e: 706(M$^+$; $C_{39}H_{50}N_2O_{10}$) |
| 1.51 | $C_2H_5$ | indole-OC(O)- | m/e: 743(M$^+$; $C_{43}H_{53}NO_{10}$) |
| 1.52 | $C_2H_5$ | 2-(methylthio)pyridine-OC(O)- | |
| 1.53 | $C_2H_5$ | N-methylpyrrole-OC(O)- | |
| 1.54 | $C_2H_5$ | 2,2-dimethyl-dioxolanone-OC(O)- | |
| 1.55 | $C_2H_5$ | imidazolidinone-OC(O)- | |
| 1.56 | $C_2H_5$ | 6,6-dimethyl-dihydropyranone-OC(O)- | |
| 1.57 | $C_2H_5$ | OC(O)C$_6$H$_4$CF$_3$(4) | |
| 1.58 | $C_2H_5$ | OC(O)CH$_2$CF$_3$ | |
| 1.59 | $C_2H_5$ | OCO—C$_6$H$_4$NO$_2$(3) | m/e: 749(M$^+$; $C_{41}H_{51}NO_{12}$) |
| 1.60 | $C_2H_5$ | OCO—C$_6$H$_4$CF$_3$(3) | m/e: 772(M$^+$; $C_{42}H_{51}F_3O_{10}$) |
| 1.61 | $C_2H_5$ | OCO—C$_6$H$_4$Br(3) | m/e: 784/782(M$^+$; $C_{41}H_{51}BrO_{10}$) |
| 1.62 | $C_2H_5$ | OCO—C$_6$H$_4$F(3) | m/e: 722(M$^+$; $C_{41}H_{51}O_{10}F$) |
| 1.63 | $C_2H_5$ | OCO—C$_6$H$_4$CH$_3$(3) | m/e: 718(M$^+$; $C_{42}H_{54}O_{10}$) |
| 1.64 | $C_2H_5$ | OCO—C$_6$H$_4$OCH$_3$(3) | m/e: 734(M$^+$; $C_{42}H_{54}O_{11}$) |
| 1.65 | $C_2H_5$ | OCOCH$_2$OH | m/e: 658(M$^+$; $C_{36}H_{50}O_{11}$) |
| 1.66 | $C_2H_5$ | OCOCH$_2$OCOCH$_3$ | m/e: 700(M$^+$; $C_{36}H_{52}O_{12}$) |

TABLE 2

Compounds of formula I (wherein $R_2 = CH_3C(O)-$)

| Comp. No. | R | $R_1$ | Physical data or reference to Example No. |
|---|---|---|---|
| 2.1 | $CH_3$ | F | m/e:660($M^+$;$C_{36}H_{49}FO_{10}$) |
| 2.2 | $CH_3$ | $CH_3$ | |
| 2.3 | $C_2H_5$ | F | |
| 2.4 | $C_2H_5$ | $CH_3$ | |
| 2.5 | $C_2H_5$ | $C_2H_5$ | |
| 2.6 | $C_2H_5$ | $C_3H_7$-n | |
| 2.7 | $C_3H_7$-i | F | |
| 2.8 | $C_3H_7$-i | $CH_3$ | |
| 2.9 | $C_4H_9$-s | F | |
| 2.10 | $C_4H_9$-s | $CH_3$ | |

Formulation Examples for active ingredients of formula I (throughout, percentages are by weight)

| Wettable powders | (a) | (b) | (c) |
|---|---|---|---|
| compound of Tables 1 and 2 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| compound of Tables 1 and 2 | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| compound of Tables 1 and 2 | 5% | 8% |
| talcum | 95% | — |
| kaolin | — | 92% |

Ready for use dusts are obtained by mixing the active ingredient with the carrier, and grinding the mixture in a suitable mill.

| Extruder granulate | |
|---|---|
| compound of Tables 1 and 2 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Tablets or boluses | |
|---|---|
| I compound of Tables 1 and 2 | 33.00% |
| methyl cellulose | 0.80% |
| highly dispersed silicic acid | 0.80% |
| maize starch | 8.40% |

The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12M sieve and the granulate is dried.

| II crystalline lactose | 22.50% |
|---|---|
| maize starch | 17.00% |
| microcrystalline cellulose | 16.50% |
| magnesium stearate | 1.00% |

All 4 adjuvants are thoroughly mixed. Phases I and II are mixed and compressed to tablets or boluses.

If the compounds of formula I, or compositions containing them, are used for controlling endoparasitic nematodes, cestodes and trematodes in domestic animals and productive livestock, for example cattle, sheep, goats, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, boluses or capsules.

If the physical and toxicological properties of solutions or emulsions permit it, the compounds of formula I, or compositions containing them, can also be injected into animals for example subcutaneously, administered intraruminally or applied to the bodies of the animals by the pour-on method. Administration by means of salt licks or molasses blocks is also possible.

Biological Examples

In the biological investigations below, the following prior art substances were tested comparatively:

(A)

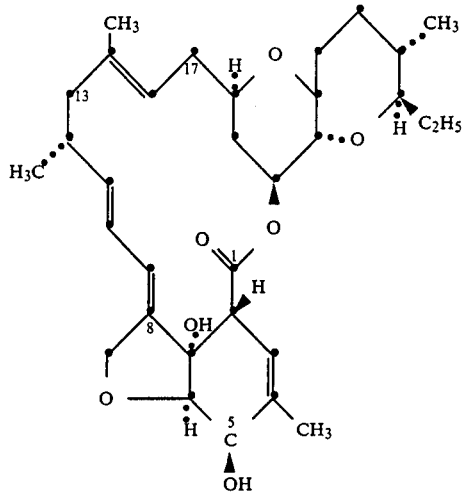

known from U.S. Pat. No. 4 468 390

(B)

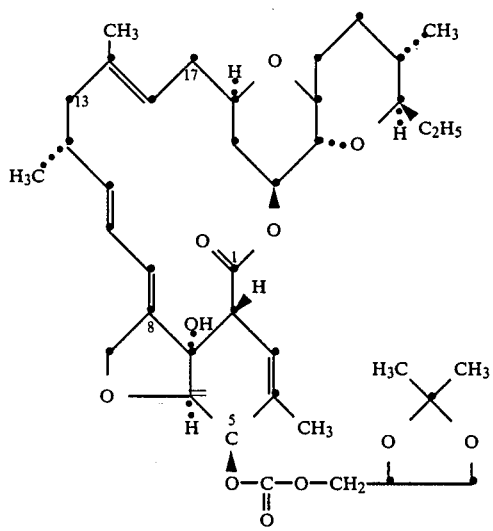

known from European patent specification 142 969

(C)

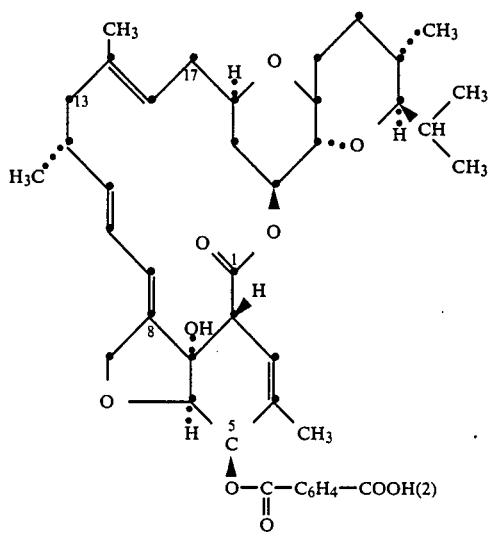

known from European patent specification 102 721

(D)

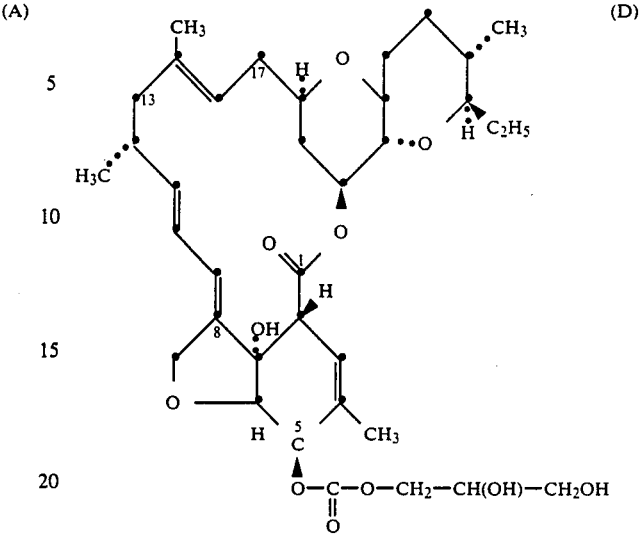

known from European patent specification 142 969

(E)

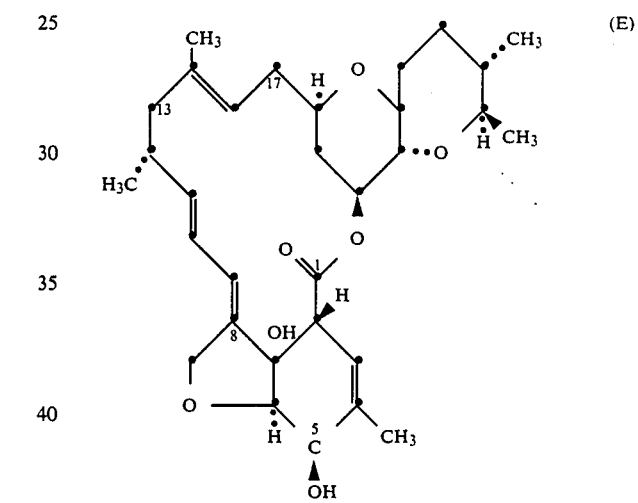

known from U.S. Pat. No. 4 468 390

B1. Trial with sheep infected with nematodes (*Haemonchus concurtus* and *Trichostronglylus colubriformis*)

The test compound is administered in the form of a suspension with a stomach probe or by intraruminal injection to sheep which have been artificially infected with Haemonchus concortus and *Trichostrongylus colubriformis*. 1 to 3 animals are used for each dose. Each sheep is treated only once with a single dose of 0.5 mg or 0.1 mg/kg of body weight. Evaluation is made by comparing the number of worm eggs excreted in the faeces of the sheet before and after treatment.

In sheep which have been treated with one of the compounds of formula I, e.g. with one of compounds 1.1, 1.2, 1.5 to 1.19, 1.21, 1.23, 1.24, 1.25 to 1.41, 1.46 to 1.51, 1.59 to 1.62, 1.65 or 2.3, at 0.5 mg/kg complete activity was achieved; at 0.1 mg/kg 80 to 100% activity was achieved. In contradistinction thereto, prior art substances (A) to (E) exhibited a completely insufficient nematicidal activity, which lay between 20 and 58%. Untreated and infected sheet were used as controls.

Evaluation was made by counting the number of worm eggs in the faeces. A complete reduction of the number of worm eggs represented 100% activity, whereas the average number of eggs in the faeces of the control animals characterised zero-activity.

What is claimed is:

1. A compound of the formula

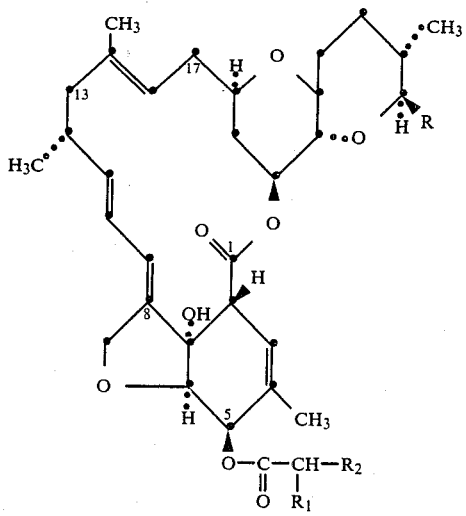

wherein
R is methyl, ethyl, isopropyl or sec-butyl;
$R_1$ is hydrogen, fluorine or $C_1-C_4$alkyl;
$R_2$ is

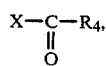

wherein
X is oxygen and
$R_4$ is hydrogen, $C_1-C_{12}$alkoxy, $C_3-C_7$cycloalkoxy or $C_2-C_6$alkenyloxy; or $C_1-C_{18}$alkyl which is unsubstituted or substituted by halogen, $C_1-C_4$alkoxy, or COOG, G being hydrogen, an alkali metal cation or an alkaline earth metal cation, or $R_4$ is $C_3-C_7$cycloalkyl which is unsubstituted or substituted by halogen or $C_1-C_4$alkyl; $C_2-C_{18}$alkenyl which is unsubstituted or substituted by halogen; $C_2-C_{18}$alkynyl which is unsubstituted or substituted by halogen; or phenyl which is unsubstituted or substituted by halogen, $C_1-C_4$alkyl, $C_1-C_4$alkoxy, nitro, cyano or $C_1-C_4$haloalkyl.

2. A compound of claim 1, wherein
$R_1$ is hydrogen, fluorine or methyl; and
$R_4$ is hydrogen, $C_1-C_4$alkoxy, $C_3-C_6$cycoalkoxy or $C_2-C_6$-alkenyloxy; or $C_1-C_6$alkyl which is unsubstituted or substituted by halogen, $C_1-C_4$alkoxy, hydroxy or COOG, G being hydrogen or an alkali metal cation; or $R_4$ is $C_3-C_6$cycloalkyl; $C_2-C_6$alkenyl which is unsubstituted or substituted by halogen; $C_2-C_6$alkynyl which is unsubstituted or substituted by halogen; or phenyl which is unsubstituted or substituted by halogen, methyl, methoxy, nitro, cyano or $CF_3$.

3. A compound of claim 2, wherein
$R_4$ is $C_1-C_4$alkoxy, $C_3-C_6$cycloalkoxy or $C_2-C_6$alkenyloxy; or $C_1-C_6$alkyl which is unsubstituted or substituted by fluorine, chlorine, $C_1-C_4$alkoxy, hydroxy or COOH; $C_3-C_6$cycloalkyl; $C_2-C_6$alkenyl which is unsubstituted or substituted by fluorine or chlorine; $C_2-C_6$alkynyl which is unsubstituted or substituted or substitued by fluorine or chlorine; or phenyl which is unsubstituted or substituted by fluorine, chlorine, methyl, methoxy, nitro, cyano or $CF_3$.

4. A compound of claim 1, selected from the group consisting of

5-O-acetoxyacetylmilbemycin D

5-O-acetoxyacetylmilbemycin $A_4$

5-O-acetoxyacetylmilbemycin $A_3$

5-O-acetoxyacetyl-13-deoxy-22,23-dihydroavermectin-B1a-aglycone

5-O-((S)-2-hydroxypropionyloxy)acetylmilbemycin D

5-O-chloroacetoxyacetylmilbemycin D 5-O-acetylthioacetylmilbemycin D 5-O-fluoroacetoxyacetylmilbemycin $A_4$ 5-O-formyloxyacetylmilbemycin $A_4$ 5-O-benzoyloxyacetylmilbemycin $A_4$ 5-O-propionyloxyacetylmilbemycin $A_4$ 5-O-methoxyacetoxyacetylmilbemycin $A_4$ 5-O-(acetoxy)fluoroacetylmilbemycin $A_4$ 5-O-(2-acetoxy)propionylmilbemycin $A_4$ 5-O-(2-acetoxy)butanoylmilbemycin $A_4$ 5-O-cyclopropylcarbonyloxyacetylmilbemycin $A_4$ 5-O-methoxycarbonyloxyacetylmilbemycin $A_4$ 5-O-(3-chlorobenzoyloxy)acetylmilbemycin D 5-O-(3-chlorobenzoyloxy)acetylmilbemycin $A_4$ 5-O-(3-chlorobenzoyloxy)acetylmilbemycin $A_3$ and 5-O-((S)-2-hydroxypropionyloxy)acetylmilbemycin $A_4$.

5. A compound of claim 1 wherein R is ethyl, $R_1$ is hydrogen, and $R_2$ is $-OC(O)CH_3$.

6. A composition for controlling parasitic pests, which composition comprises the compound of claim 5 in a pesticidally effective amount and at least one inert adjuvant.

7. A method of controlling pests of productive livestock and plants, which method comprises applying to the animal, the plant or to the locus thereof a pesticidally effective amount of the compound of claim 5.

8. A composition for controlling parasitic pests, which composition contains a pesticidally effective amount of a compound of the formula

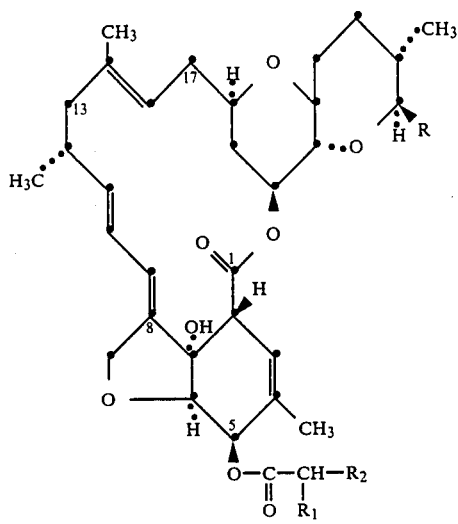

wherein
R is methyl, ethyl, isopropyl or sec-butyl;
$R_1$ is hydrogen, fluorine or $C_1-C_4$alkyl;
$R_2$ is

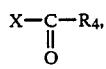

wherein
X is oxygen and
$R_4$ is hydrogen, $C_1-C_{12}$alkoxy, $C_3-C_4$cycloalkoxy or $C_2-C_6$alkenyloxy; or $C_1-C_{18}$alkyl which is unsubstituted or substituted by halogen, $C_1-C_4$alkoxy, hydroxy, or COOG, G being hydrogen, an alkali metal cation or an alkaline earth metal cation, or $R_4$ is $C_3-C_7$cycloalkyl which is unsubstituted or substituted by halogen or $C_1-C_4$alkyl; $C_2-C_{18}$alkenyl which is unsubstituted or substituted by halogen; $C_2-C_{18}$alkynyl which is unsubstituted or substituted by halogen; or phenyl which is unsubstituted or substituted by halogen, $C_1-C_4$alkyl, $C_1-C_4$alkoxy, nitro, cyano or $C_1-C_4$haloalkyl.

9. A method of controlling pests of productive livestock and plants, which method comprises applying to the animal, to the plant or to the locus thereof a pesticidally effective amount of a compound of the formula

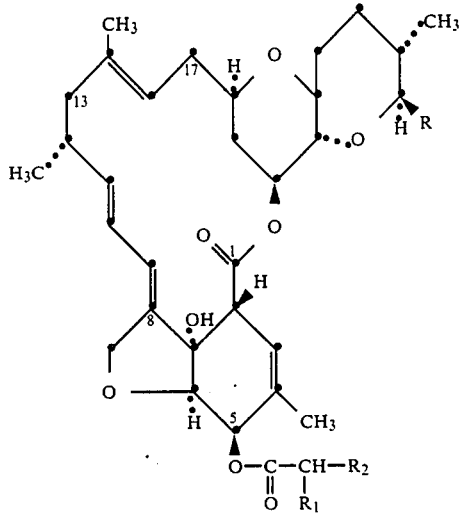

wherein
R is methyl, ethyl, isopropyl or sec-butyl;
$R_1$ is hydrogen, fluorine or $C_1-C_4$alkyl;
$R_2$ is

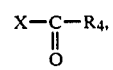

wherein
X is oxygen and
$R_4$ is hydrogen, $C_1-C_{12}$alkoxy, $C_3-C_7$cycloalkoxy or $C_2-C_6$alkenyloxy; or $C_1-C_{18}$alkyl which is unsubstituted or substituted by halogen, $C_1-C_4$alkoxy, hydroxy, or COOG, G being hydrogen, an alkali metal cation or an alkaline earth metal cation, or $R_4$ is $C_3-C_7$cycloalkyl which is unsubstituted or substituted by halogen or $C_1-C_4$alkyl; $C_2-C_{18}$alkenyl which is unsubstituted or substituted by halogen; $C_2-C_{18}$alkynyl which is unsubstituted or substituted by halogen; or phenyl which is unsubstituted or substituted by halogen, $C_1-C_4$alkyl, $C_1-C_4$alkoxy, nitro, cyano or $C_1-C_4$haloalkyl.

10. A method according to claim 9 for controlling endoparasites in productive livestock.

11. A method according to claim 10, wherein the endoparasites are nematodes.

* * * * *